Figure 1:
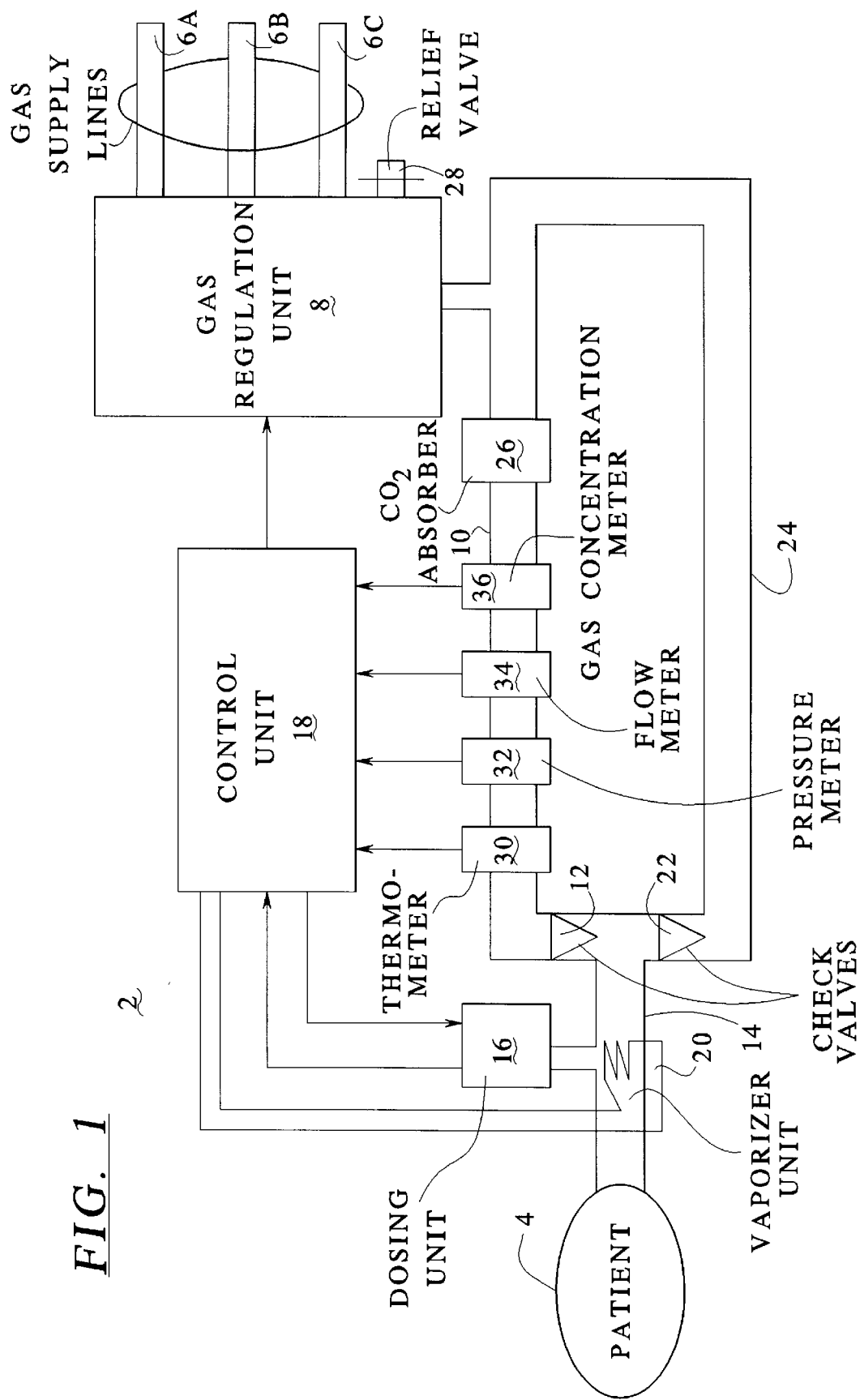

United States Patent [19]

Psaros et al.

[11] Patent Number: 5,771,882

[45] Date of Patent: Jun. 30, 1998

[54] ANESTHETIC ADMINISTRATION APPARATUS WHICH DELIVERS ANESTHETIC IN MICRODROPLETS

[75] Inventors: Georgios Psaros, Tullinge; Rolf Castor, Hägersten, both of Sweden

[73] Assignee: Siemens Elema AB, Solna, Sweden

[21] Appl. No.: 711,654

[22] Filed: Sep. 9, 1996

[30] Foreign Application Priority Data

Sep. 12, 1995 [SE] Sweden .................................. 9503141

[51] Int. Cl.$^6$ .................................................. A61M 15/00
[52] U.S. Cl. ............................... 128/203.12; 128/200.14; 128/203.14
[58] Field of Search ........................ 128/200.14, 200.16, 128/202.22, 203.12, 203.14

[56] References Cited

U.S. PATENT DOCUMENTS

| | | | |
|---|---|---|---|
| 3,812,854 | 5/1974 | Michaels et al. .................. | 128/200.16 |
| 4,308,865 | 1/1982 | Hay .................................. | 128/200.14 |
| 4,611,590 | 9/1986 | Ryschka et al. .................... | 128/203.14 |
| 5,072,726 | 12/1991 | Mazloomdoost et al. ......... | 128/200.14 |
| 5,080,093 | 1/1992 | Raabe et al. ...................... | 128/203.12 |
| 5,287,849 | 2/1994 | Piper et al. ........................ | 128/203.12 |
| 5,309,903 | 5/1994 | Long .................................. | 128/203.12 |
| 5,349,946 | 9/1994 | McComb .......................... | 128/203.12 |
| 5,423,313 | 6/1995 | Olsson et al. ..................... | 128/204.21 |
| 5,487,378 | 1/1996 | Robertson et al. ................ | 128/200.14 |
| 5,497,944 | 3/1996 | Weston et al. .................... | 128/203.12 |
| 5,546,931 | 8/1996 | Rusz .................................. | 128/203.14 |

FOREIGN PATENT DOCUMENTS

| | | |
|---|---|---|
| 0 243 259 | 10/1987 | European Pat. Off. . |
| 0 692 273 | 1/1996 | European Pat. Off. . |
| WO 95/01137 | 1/1995 | WIPO . |

*Primary Examiner*—Aaron J. Lewis
*Attorney, Agent, or Firm*—Hill & Simpson

[57] ABSTRACT

An anesthetic apparatus has a dosing unit for an anesthetic agent, the dosing unit having a number of containers, each holding a liquid anesthetic agent. The containers are connected by liquid lines to a valve unit, capable of selectively connecting one container at a time to a micropump which dispenses anesthetic in the form of liquid droplets directly to a connection piece in the anesthetic apparatus, to which a patient can be connected. A control unit controls the micropump and the valve unit and regulates both the selection and dispensing of liquid anesthetic.

10 Claims, 2 Drawing Sheets

ANESTHETIC ADMINISTRATION APPARATUS WHICH DELIVERS ANESTHETIC IN MICRODROPLETS

BACKGROUND OF THE INVENTION

1. Field of the Invention

The present invention is directed to an apparatus for administering anesthetic to a subject, as well as to a medication nebulizer.

2. Description of the Prior Art

Swedish Published Application 430 213 describes a respirator having a respiratory circuit with an inspiratory line, an expiratory line and a tracheal tube for connecting the respirator to a patient. Gas can be carried from a first source of gas in the respirator to the patient in the inspiratory line and tracheal tube. Gas can also be supplied from a second source of gas, directly to the tracheal tube, through a separate gas line. An anesthetic gas can, inter alia, be carried directly to the connecting line. Gas can be supplied continuously or according to a specific pattern, e.g. during an initial part of an inspiration. Gas flows are regulated with valves controlled by a control device.

Regulating these valves, however, can be rather complicated, since the control of gases and gas flows is involved. All the lines create flow resistances and compressible spaces. Gas flows from two lines (the inspiratory line and the separate gas line) must be coordinated and even made to mix. A simpler, more reliable and more easily controlled anesthetic apparatus for supplying anesthetic gas to a living creature is desirable.

SUMMARY OF THE INVENTION

An object of the present invention is to provide an anesthetic apparatus which eliminates the above-described problems.

The above object is achieved in accordance with the principles of the present invention in an apparatus for administering anesthetic to a subject having a respiratory circuit through which a respiratory gas, containing a defined amount of an anesthetic, is supplied to a subject during an inspiratory phase, a dosing unit for supplying liquid anesthetic to a connection piece in the respiratory circuit, the connection piece being directly connectable to the subject, and the dosing unit including a container for the liquid anesthetic and a micropump for supplying the liquid anesthetic in microdroplets to the connection piece, the micropump being controlled by a control unit.

Instead of supplying gaseous anesthetic to the respiratory circuit, the anesthetic is supplied in droplets by means of a micropump. In other words, it is supplied in the form of microdroplets, preferably less than 100 nm in diameter. This makes it possible for supply to take place inside the connection means, i.e. very close to the patient. The tiny microdroplets are rapidly vaporized in the connection means. The concentration of anesthetic can be varied rapidly and reliably when anesthetic is supplied. No additional gas lines, with attendant resistances to flow and compressibility, are needed.

The micropump appropriately consists of a piezoelectric pump. Such pumps are well-known in the ink jet art and do not require any detailed description. The liquid anesthetic's physical properties, such as its molecular weight, vapour pressure, surface tension and heat of vaporization, are programmed into the micropump's control unit. The size of droplets can then be regulated with extreme accuracy. So dispensing is accordingly very exact.

In the same way as is known in the art, anesthetic can be supplied during part of a breathing cycle, e.g., during an initial part of the inspiratory phase.

The micropump's exact dosing capability makes it excellent for dispensing liquids other than liquid anesthetics, in particular, liquid medication which must be supplied to the patient in exact amounts in the respiratory gas. A very accurate nebulizer can therefore be achieved.

In one embodiment of the anesthetic apparatus, the supply of anesthetic can be regulated based on the measured momentary flow of respiratory gas and a reference value for the end concentration of anesthetic. Control can be refined by e.g. taking the temperature and pressure of the respiratory gas and the temperature of the liquid anesthetic into account. These parameters can be measured and/or regulated to achieve predetermined values. The end concentration can also be controlled by a concentration meter.

To facilitate vaporization of the droplets of liquid anesthetic, a vaporizer can be located in the connection means such that droplets from the micropump fall onto this vaporizer are evaporated. The temperature of the vaporizer means can be regulated according to the liquid anesthetic's vaporization characteristics.

A number of containers holding different liquid anesthetics can be arranged in parallel in the dosing unit and connected to the micropump via a valve unit which only permits the release of liquid anesthetic from one container at a time. This makes it possible to switch anesthetic agents rapidly and to achieve a dosing unit which is much smaller than known anesthetic vaporizers.

DESCRIPTION OF THE DRAWINGS

FIG. 1 is a block diagram of a first embodiment of the anesthetic apparatus according to the invention.

FIG. 2 is a block diagram of a dosing unit in the inventive anesthetic apparatus.

FIG. 3 is a block diagram of a second embodiment of the anesthetic apparatus according to the invention.

DESCRIPTION OF THE PREFERRED EMBODIMENTS

The anesthetic apparatus 2 in FIG. 1 is connected to a patient 4 in order to supply the patient 4 with a respiratory gas and an anesthetic. The respiratory gas is prepared by connecting the anesthetic apparatus 2 to a first gas connection 6A, a second gas connection 6B and a third gas connection 6C. The components of the respiratory gas, such as oxygen ($O_2$) and nitrous oxide ($N_2O$) , are carried via the gas connections to a gas regulation unit 8. The supplied gas components are mixed in specific proportions in the gas regulation unit 8.

The respiration rhythm of the patient 4 (respiratory depth and respiration rate) is also regulated via the gas regulation unit 8. Thus, respiratory gas is supplied to the patient 4 through an inspiratory line 10 and a connection piece 14. A first check (one-way) valve 12 is arranged in the inspiratory line 10 to control the direction of flow of the respiratory gas. The connection piece 14 can consist of a tracheal tube or the equivalent.

A dosing unit 16 is connected to the connection piece 14 in order to supply anesthetic in the form of liquid droplets. The dosing unit 16, which will be described below in greater detail, is controlled by a control unit 18, which also controls the gas regulation unit 8. The dosing unit 16 pumps out anesthetic in droplet form onto a vaporizer unit 20 to facilitate the vaporization of the anesthetic before, it is carried with respiratory gas down into the lungs of the patient 4.

The temperature of the vaporizer unit 20 can be regulated by the control unit 18.

In expiration, respiratory gas is carried through an expiratory line 24 back to the gas regulation unit 8. A second check valve 22 is arranged in the expiratory line 24 to control the direction of flow.

The anesthetic apparatus 2 operates as a closed circuit system. This means that as much of the respiratory gas as possible is re-used after expiration. A carbon dioxide absorber 26 is therefore arranged in the inspiratory line 10 to absorb carbon dioxide expired by the patient 4. A pressure relief valve 28 is also arranged in the gas regulation unit 8 to keep the pressure of gas in the respiratory circuit from exceeding a predefined value (surplus gas is bled by the pressure relief valve 28 if that predefined pressure is reached). Since the system is closed, a minimal amount of fresh gas is supplied through the gas connections 6A, 6B and 6C during surgery, however, the flow of fresh respiratory gas is much larger during the induction of narcosis and recovery from same.

Control of the supply of respiratory gas is refined by the measurement of a number of parameters for respiratory gas in the inspiratory line 10 and taken into account in the dispensing effected by the control unit 18. For this purpose, temperature is measured in a first thermometer 30, pressure in a pressure meter 32, momentary flow in a flow meter 34 and concentration in a gas meter 36.

Figure 2:
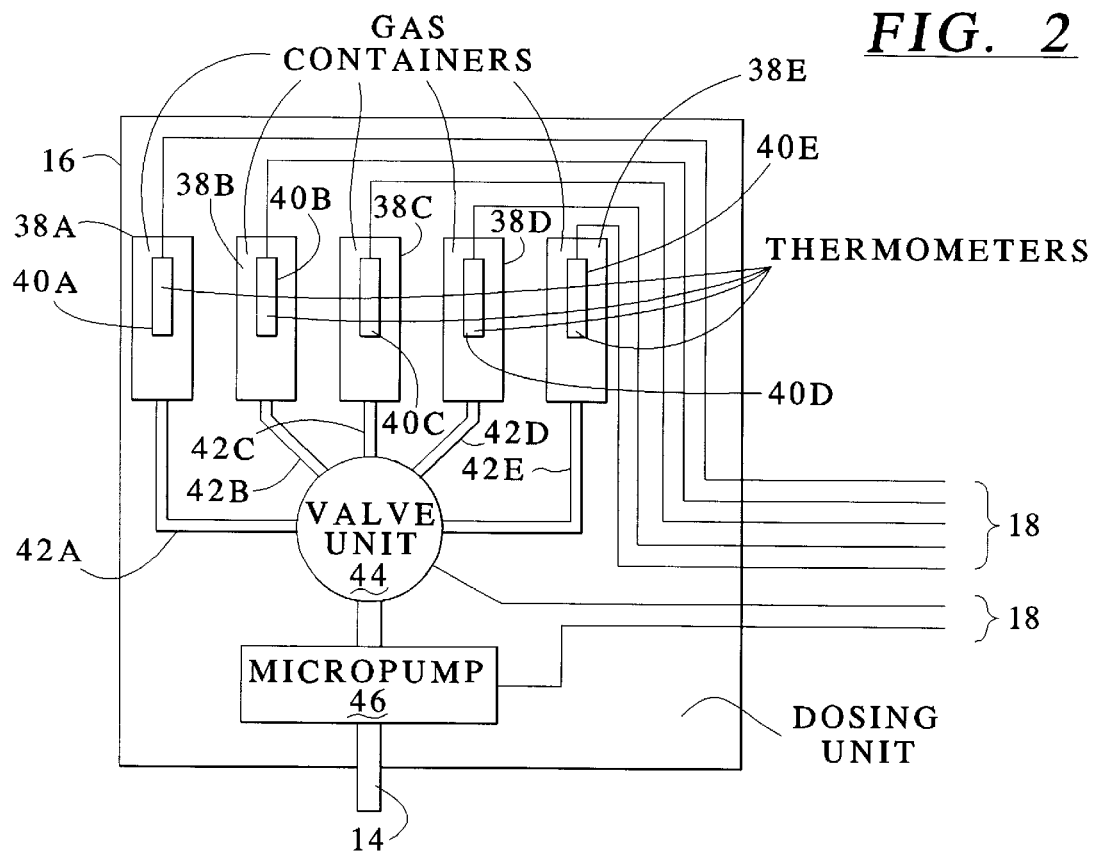

Dispensing will now be described in greater detail, referring to the dosing unit 16 in FIG. 2. The dosing unit 16 has a first container 38A for a first anesthetic, a second container 38B for a second anesthetic, a third container 38C for a third anesthetic, a fourth container 38D for a fourth anesthetic and a fifth container 38E for a fifth anesthetic. The anesthetics are in liquid form and may be halothane, enflurane, desflurane, isoflurane and sevoflurane.

A second thermometer 40A is arranged in the first container 38A to measure the temperature of the first liquid anesthetic, a third thermometer 40B is arranged in the second container 38B to measure the temperature of the second liquid anesthetic, a fourth thermometer 40C is arranged in the third container 38C to measure the temperature of the third liquid anesthetic, a fifth thermometer 40D is arranged in the fourth container 38D to measure the temperature of the fourth liquid anesthetic and a sixth thermometer 40E is arranged in the fifth container 38E to measure the temperature of the fifth liquid anesthetic. Measured temperatures are transferred to the control unit 18. The thermometers 40A, 40B, 40C, 40D, 40E may alternatively be temperature regulators for regulating the temperatures of the liquid anesthetic at the predefined temperature for each liquid anesthetic.

A first liquid line 42A from the first liquid container 38A leads, to a valve unit 44, a second liquid line 42B from the second container 38B leads to the valve unit 44, a third liquid line 42C from the third container 38C leads to the valve unit 44, a fourth liquid line 42D from the fourth container 38D leads to the valve unit 44 and a fifth liquid line 42E from the fifth container 38E leads to the valve unit 44. The valve unit 44 is devised so only one liquid line 42A, 42B, 42C, 42D, 42E at a time can release liquid to a micropump 46. The micropump 46 pumps out liquid anesthetic in the form of microdroplets, preferably less than 100 nm in diameter. Both the valve unit 44 and the micropump 46 are controlled by the control unit 18. The micropump 46 is preferably a piezoelectric pump.

Figure 3:
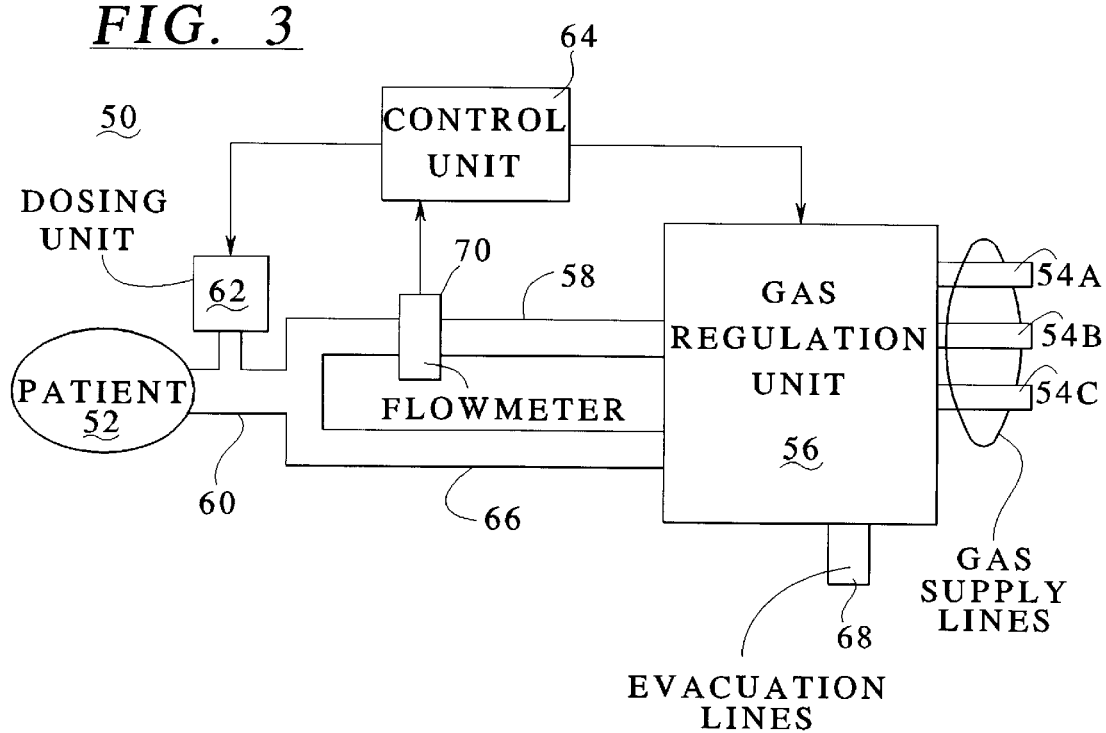

FIG. 3 shows a second embodiment of the anesthetic apparatus, designated 50, according to the invention. The anesthetic apparatus 50, which is connected to a patient 52, operates as an open system, i.e. no gas is re-used. The gas components in the respiratory gas are sent to the anesthetic apparatus 50 through a first gas connection 54A, a second gas connection 54B and a third gas connection 54C. As in the previous embodiment, the gas components can be $O_2$ and $N_2O$. The gas components are mixed in specific proportions in a gas regulation unit 56 which also regulates the pressure and flow of respiratory gas supplied to the patient 52.

Here, the respiratory gas passes through an inspiratory line 58 and a connection piece 60 to the patient 52. A dosing unit 62 (as shown in FIG. 2) is connected to the connection piece 60 to supply it with anesthetic in droplet form. The droplets are so small and the flow of respiratory gas is so fast that the droplets vaporize before they reach the lungs of the patient 52. Anesthetic is only supplied during part of each inspiratory phase, since the relative concentration in the lungs is sufficient to sustain the desired depth of anesthesia in the patient 52. The consumption of anesthetic is therefore considerably lower than in other known open systems in which anesthetic gas is mixed with respiratory gas at an earlier stage.

In expiration, respiratory gas passes through an expiratory line 66 before it returns to the gas regulation unit 56 for discharge through the evacuation line 68 into some form of gas collection vessel or filter device.

The dispensing of anesthetic droplets is regulated by a control unit 64 according to the value measured for the momentary flow of respiratory gas in the inspiratory line 58. Flow is measured in a flowmeter 70. The control unit also controls the gas regulation unit 56.

The anesthetic apparatus according to the invention can also be devised for semiopen or semi-closed systems, or combinations of such systems and the described embodiments. Instead of a dosing unit with a number of containers, a number of dosing units, each of which with one or more containers, can be connected to the connection means.

Instead of dispensing a liquid anesthetic, the dosing unit 62 in FIG. 3 can dispense some other liquid with the same accuracy. In particular, it can dispense nebulized medication. The micropump is capable of generating liquid droplets so small that the dosing unit 62 is able to operate as a nebulizer. The design of such a micropump nebulizer can be identical to the design of the dosing unit according to FIG. 2, i.e. it can contain a number of liquid containers. In this instance, a number of different drugs can be used in turn, or a single drug can be used in different concentrations.

Although modifications and changes may be suggested by those skilled in the art, it is the intention of the inventors to embody within the patent warranted hereon all changes and modifications as reasonably and properly come within the scope of their contribution to the art.

We claim as our invention:

1. An anesthetic administration apparatus comprising:
   a respiratory circuit including a connection piece directly connectable to a respirating subject to be anesthetized for carrying respiratory gas to and from a subject;
   a dosing unit connected to said connection piece and supplying liquid anesthetic to said connection piece, said dosing unit including a container containing said liquid anesthetic, and a micropump in fluid communication with said container for supplying said liquid anesthetic in microdroplets to said connection piece; and control means for operating said micropump for causing said micropump to deliver a predetermined amount of said liquid anesthetic in microdroplets during an inspiratory phase of a subject.

2. An apparatus as claimed in claim 1 wherein said micropump comprises a micropump which delivers said microdroplets in a size of less than 100 nm in diameter.

3. An apparatus as claimed in claim 1 wherein said micropump comprises a piezoelectric pump.

4. An apparatus as claimed in claim 1 wherein said control means comprises means for regulating a release of anesthetic by said micropump only during a part of said inspiratory phase.

5. An apparatus as claimed in claim 1 wherein said respiratory circuit includes an inspiratory line, and said apparatus further comprising a flow meter disposed in said inspiratory line for determining a value of a momentary flow of respiratory gas to said subject and for supplying a signal corresponding to said momentary flow to said control means, and wherein said control means comprises means for regulating a release of said liquid anesthetic by said micropump dependent on said momentary flow value relative to a predetermined reference value, said reference value corresponding to a desired concentration of anesthetic in the respiratory gas.

6. An apparatus as claimed in claim 1 further comprising:

a first thermometer disposed in said respiratory circuit and generating a first signal identifying a temperature of said respiratory gas in said respiratory circuit;

a second thermometer disposed in said container and emitting a second signal identifying a temperature of said liquid anesthetic in said container;

a pressure meter disposed in said respiratory circuit and emitting a third signal identifying a pressure of said respiratory gas in said respiratory circuit; and wherein said control means comprises means for controlling a release of said liquid anesthetic by said micropump dependent on said first, second and third signals.

7. An apparatus as claimed in claim 1 further comprising heatable vaporizer means, disposed in said connection piece, for vaporizing said liquid anesthetic from said micropump.

8. An apparatus as claimed in claim 7 wherein said control means is connected to said vaporizing means and wherein said control means comprises means for regulating a temperature of said vaporizing means dependent on vaporization properties of said liquid anesthetic.

9. An apparatus as claimed in claim 1 wherein said dosing unit further includes at least one additional container containing an additional liquid anesthetic, and valve means connecting said container and said additional container to said micropump for permitting only one of said container or said additional container to supply liquid anesthetic at a time to said micropump.

10. An apparatus as claimed in claim 1 further comprising a gas meter, disposed in said respiratory circuit, which measures a concentration of anesthetic in said respiratory gas and which emits a gas meter signal corresponding thereto, and wherein said control unit comprises means for controlling said micropump dependent on said gas meter signal.

* * * * *